(12) United States Patent
Kato

(10) Patent No.: US 8,999,128 B2
(45) Date of Patent: Apr. 7, 2015

(54) REFERENCE ELECTRODE AND ION CONCENTRATION MEASUREMENT DEVICE

(75) Inventor: Makoto Kato, Kyoto (JP)

(73) Assignee: Horiba, Ltd. (JP)

( * ) Notice: Subject to any disclaimer, the term of this patent is extended or adjusted under 35 U.S.C. 154(b) by 138 days.

(21) Appl. No.: 13/594,048

(22) Filed: Aug. 24, 2012

(65) Prior Publication Data

US 2013/0056351 A1 Mar. 7, 2013

(30) Foreign Application Priority Data

Sep. 2, 2011 (JP) .................................. 2011-191304

(51) Int. Cl.
*G01N 27/26* (2006.01)
*C25B 9/04* (2006.01)
*C25B 11/00* (2006.01)
*G01N 27/30* (2006.01)

(52) U.S. Cl.
CPC .................................. *G01N 27/301* (2013.01)

(58) Field of Classification Search
CPC .......... C25C 7/02; C25B 11/00; G01N 27/30; G01N 27/301; G01N 27/302; G01N 27/36; G01N 37/333
USPC ................. 204/435, 280, 288.1, 229.8, 230.1
See application file for complete search history.

(56) References Cited

U.S. PATENT DOCUMENTS

| | | | | |
|---|---|---|---|---|
| 4,659,451 A | * | 4/1987 | Fujita et al. ................... | 204/435 |
| 7,186,325 B2 | * | 3/2007 | Osterbrink et al. ........... | 204/408 |
| 2003/0168354 A1 | * | 9/2003 | Broadley et al. .............. | 205/775 |

FOREIGN PATENT DOCUMENTS

| | | |
|---|---|---|
| JP | 54131994 A | 10/1979 |
| JP | 59190648 A | 10/1984 |
| JP | 60260840 A | 12/1985 |
| JP | 2005-77252 A | 3/2005 |

OTHER PUBLICATIONS

Machine Translation of JP 2005-077252A.*
Japanese Office Action issued in Japanese Patent Application No. 2011-191304; Dated Dec. 18, 2014, with English summary.

* cited by examiner

*Primary Examiner* — Edna Wong
*Assistant Examiner* — Alexander W Keeling
(74) *Attorney, Agent, or Firm* — Cantor Colburn LLP

(57) ABSTRACT

This invention prevents leakage of an internal liquid and breakage of a reference electrode resulting from volume expansion of the internal liquid due to the congelation of the internal liquid, and comprises a vessel that forms a sealed space, an internal liquid that is contained in the vessel, an internal electrode that is immersed in the internal liquid, an ion conduction part that is arranged on a wall of the vessel and that electrically connects the internal liquid and a measurement sample, and a volume expansion absorption mechanism 6 at least a part of which is immersed in the internal liquid and that absorbs volume expansion of the internal liquid due to congelation of the internal liquid.

5 Claims, 5 Drawing Sheets

REFERENCE ELECTRODE AND ION CONCENTRATION MEASUREMENT DEVICE

FIELD OF THE ART

This invention relates to a reference electrode.

BACKGROUND ART

As a conventional reference electrode conceived is a reference electrode that comprises, as shown in the patent document 1, a vessel where a liquid junction and a venthole are formed, an internal liquid contained in the vessel, an internal electrode immersed into the internal liquid, and a pressure adjust layer that locates between the internal liquid and the venthole and that transforms in accordance with a pressure.

Under a condition of being used at a high temperature, the reference electrode prevents a pressurized state due to thermal expansion of the air in the vessel or water vapor vaporized from the internal liquid so as to prevent the internal liquid from leaking out from the liquid junction. In addition, under a condition of being used at a low temperature, the reference electrode prevents a negative-pressurized state due to thermal shrinkage of the air in the vessel and liquefaction of the water vapor so as to prevent the air from entering into the vessel through the liquid junction part.

However, although it is possible for the reference electrode having the above-mentioned arrangement to solve the problem associated with the expansion and shrinkage of the air in the vessel resulting from the temperature at which the reference electrode is used, it is not possible for the reference electrode having the above-mentioned arrangement to solve the problem associated with the volume expansion of the internal liquid due to congelation of the internal liquid generating at a time when the reference electrode is kept at a low temperature. In other words, there are problems such that the internal liquid leaks from the liquid junction part and a boundary between the liquid junction part and the vessel, the liquid junction part is separated from the vessel and a crack is formed on the boundary between the liquid junction part and the vessel due to volume expansion of the internal liquid due to congelation of the internal liquid. Especially, in case that the reference electrode is kept in a standing state, the lower a position of the internal liquid is, the higher a concentration of the internal liquid becomes. As a result of this, the internal liquid gradually freezes from the upper surface. Then, the lower a position of the vessel is, the bigger the influence of the volume expansion is. As a result, since the inner pressure of the liquid junction part or its vicinity becomes high, it is likely to cause the above-mentioned problems.

Then it can be conceived that the internal liquid is prevented from freezing by adding an anti-freezing agent in the internal liquid, however, there are problems that not only an adverse effect is caused on the liquid junction potential by the anti-freezing agent but also a sample is contaminated by the anti-freezing agent that leaks into the sample together with the internal liquid.

PRIOR ART DOCUMENT

Patent Document

Patent document 1: Japanese Unexamined Patent Application Publication No. 2005-77252

DISCLOSURE OF THE INVENTION

Problems to be Solved by the Invention

A main object of this invention is to prevent leakage of the internal liquid and breakage of the reference electrode resulting from volume expansion of the internal liquid due to congelation of the internal liquid.

Means to Solve the Problems

More specifically, the reference electrode in accordance with this invention is characterized by comprising a vessel that forms a sealed space, an internal liquid that is contained in the vessel, an internal electrode that is immersed in the internal liquid, an ion conduction part that is arranged on a wall of the vessel and that electrically connects the internal liquid and a measurement sample, and a volume expansion absorption mechanism at least a part of which is immersed in the internal liquid and that absorbs volume expansion of the internal liquid due to congelation of the internal liquid.

In accordance with this arrangement, since the volume expansion of the internal liquid due to congelation of the internal liquid is absorbed by the volume expansion absorption mechanism at least a part of which is immersed in the internal liquid, it is possible to prevent leakage of the internal liquid and breakage of the reference electrode resulting from congelation of the internal liquid.

It is preferable that a concrete embodiment of the volume expansion absorption mechanism is a hollow body having an elastic transform part at least a part of which is immersed in the internal liquid and that makes an elastic transformation in accordance with the volume expansion of the internal liquid and a gaseous layer that is arranged to make contact with the elastic transform part. In accordance with this arrangement, since at least a part of the elastic transform part is immersed in the internal liquid, in case that a volume of the internal liquid expands due to congelation of the internal liquid, the elastic transform part is pushed to the gaseous layer side by the volume expansion and an amount of the expanded volume is absorbed by the gaseous layer. In addition, if the hollow body is arranged in the sealed vessel separately from the vessel, there is no need of providing a special process for the volume expansion absorption mechanism just by housing the hollow body in the vessel together with the internal liquid.

In order to make it possible for whole of the hollow body to absorb the volume expansion due to congelation of the internal liquid, it is preferable that the hollow body is a bag-shaped elastic body inside of which a gas is filled.

It is preferable that the bag-shaped elastic body is an elastic tube that is arranged from one end part of the sealed space in the vessel to the other end part thereof and both ends of which are blocked. Since the elastic tube is arranged from one end part of the sealed space in the vessel to the other end part thereof, it is possible to absorb the volume expansion that generates on each part of the internal liquid that freezes stepwise.

In order to preferably absorb the volume expansion due to congelation of the internal liquid in a limited sealed space, it is preferable that a plurality of the elastic tubes are arranged in the sealed space.

In this invention, it is preferable that the ion conduction part comprises a gelatinized ionic liquid. In case that the ionic liquid is used, since it is possible to obtain an electric potential stability without leaking the internal liquid to outside, there is no need of using a KCl solution of a high concentration (3.3 M) so that the concentration of the internal liquid can be lowered. In case that the internal liquid of a low concentration (for example 0.01 M~3.0 M) is used, since a coagulation point of the internal liquid rises and comes to a zero point, the internal liquid easily freezes. As mentioned, in case that the ionic liquid that can make the concentration of the internal liquid low is used as the ion conduction part, it is possible to further distinguish the effect of this invention. In addition, since the gelatinized ionized liquid is used for the ion conduction part, it is possible to minimize the pollution of the sample solution and to remove a fluctuation of the liquid junction potential between the internal liquid of the reference electrode and the sample solution almost completely. In addition, since the internal liquid does not easily decrease or the concentration of the internal liquid does not easily become low, a frequency of refilling or exchanging the internal liquid can be reduced.

Effect of the Invention

In accordance with the presently claimed invention having the above arrangement, since the volume expansion of the internal liquid due to congelation of the internal liquid is absorbed by the volume expansion absorption mechanism at least a part of which is immersed in the internal liquid, it is possible to prevent leakage of the internal liquid and breakage of the reference electrode resulting from congelation of the internal liquid.

BEST MODES OF EMBODYING THE INVENTION

Figure 1:
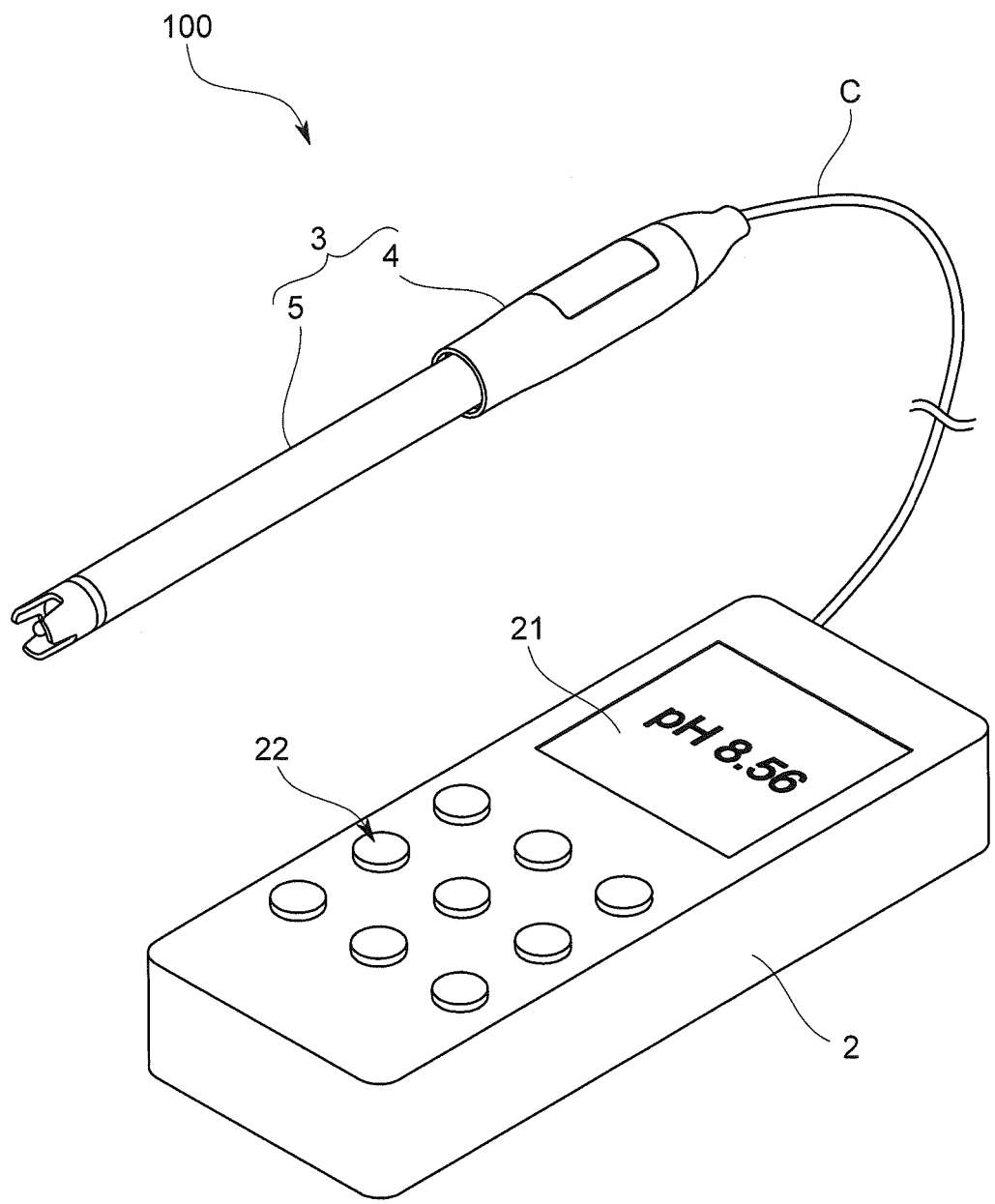
FIG. 1 is a perspective view showing an overall structure of an ion concentration measurement device in accordance with this embodiment.

One embodiment of an ion concentration measurement device using a composite electrode of this invention will be explained with reference to drawings. The ion concentration measurement device 100 of this embodiment has, as shown in FIG. 1, a device body 2 and a probe 3, each of which is detachable through a signal cable (C). The device body 2 comprises a display part 21 and an operating part 22, and measures various ion concentrations depending on a kind of the probe 3 to be connected and displays the measurement result on a display part 21. FIG. 1 shows a case of measuring a pH of a measurement sample, however, other ion concentration may be measured.

The probe 3 has a probe body 4 from which the signal cable (C) extends to the outside, and a composite electrode 5 that is mounted on the probe body 4 in a detachable manner.

Figure 2:
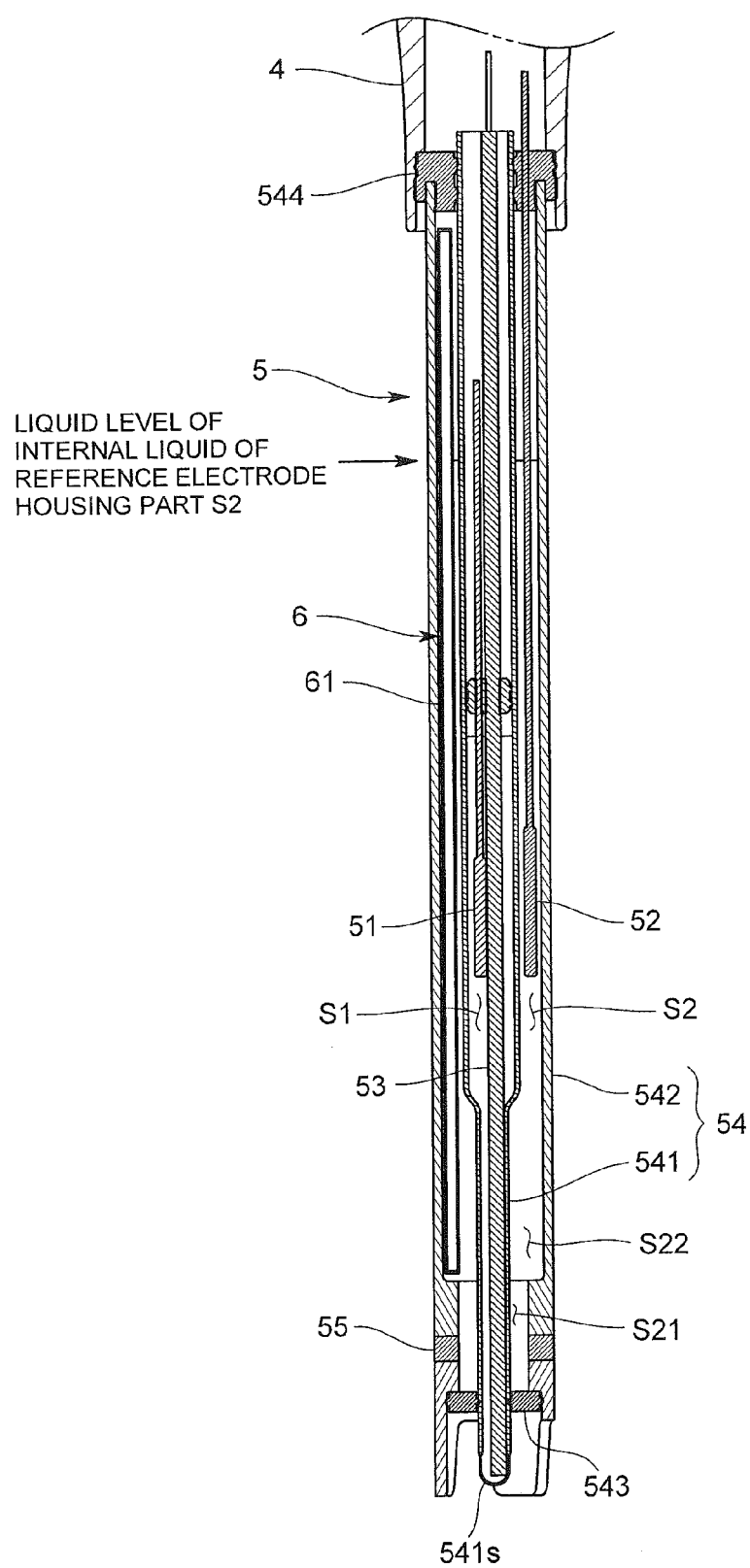
FIG. 2 is a cross-sectional view along an axial direction of a composite electrode of this embodiment.

The composite electrode 5 is, for example, of an internal liquid non-replenish type, and has an ion selective electrode such as, for example, a pH electrode to measure a predetermined ion concentration such as a hydrogen-ion concentration in a measurement sample, a reference electrode and a temperature compensated electrode, all of which are integrally formed. The composite electrode 5 has, as shown in FIG. 2, an internal electrode 51 for the ion-selective electrode, an internal electrode 52 for the reference electrode, a temperature detecting element 53 such as a thermister constituting a temperature compensated electrode, and a support tube 54 to be a vessel that forms a sealed space housing the internal electrode 51 for the ion-selective electrode, the internal electrode 52 for the reference electrode and the temperature detecting element 53. The temperature detecting element 53 outputs an electrical signal according to the temperature.

An inside of the support tube 54 is divided into an ion-selective electrode housing part S1 that houses the internal electrode 51 for the ion-selective electrode and the temperature detecting element 53, and a reference electrode housing part S2 that houses the internal electrode 52 for the reference electrode. Concretely, the support tube 54 has an inner tube 541 made of glass that forms the ion-selective electrode housing part S1 and an outer tube 542 that forms the reference electrode housing part S2 between the side peripheral wall of the inner tube 541 and the outer tube 542. A hemispherical dome-shaped part at a distal end part of the inner tube 541 is a glass response film 541s.

The outer tube 542 surrounds the side peripheral wall of the inner tube 541 so as to expose the glass response film 541s of the inner tuber 541 to the outside, and a distal end part of the outer tuber 542 is blocked by a sealing member 543 so as to make the reference electrode housing part S2 as a sealed space. A rear end part of the inner tube 541 and a rear end part of the outer tuber 542 are also blocked by the sealing member 544. With this arrangement, a sealed space is formed between the inner tube 541 and the outer tube 542.

Figure 3:
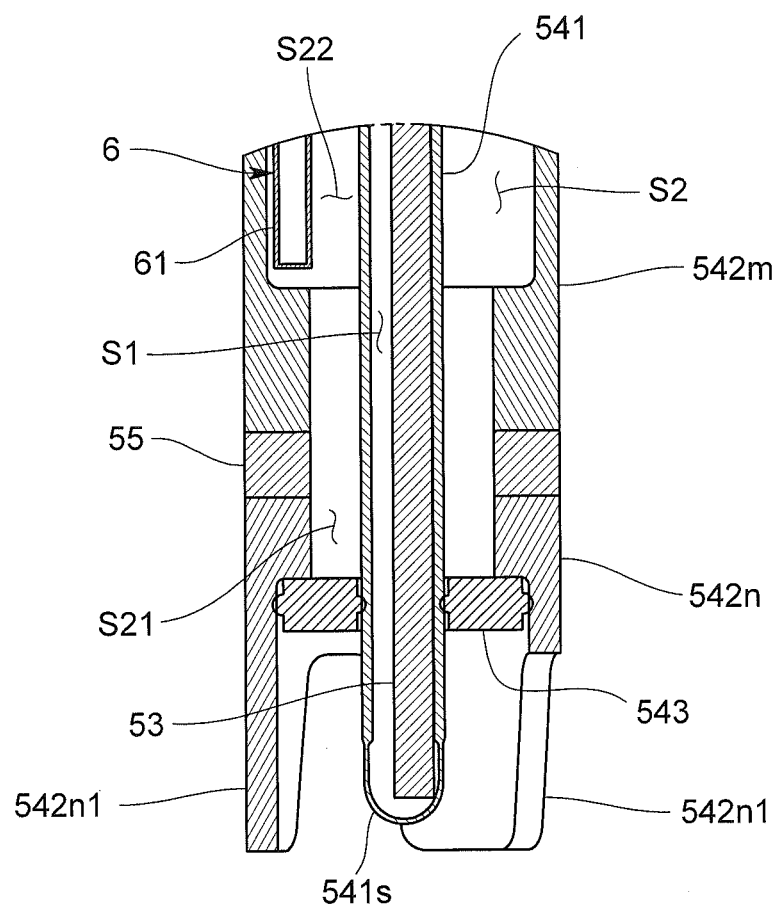
FIG. 3 is an enlarged cross-sectional view showing a distal end part of the composite electrode of this embodiment.

Furthermore, at the distal end part of the outer tuber 542 arranged is an ion conduction part 55 to electrically connect the inner liquid and the measurement sample. The ion conduction part 55 of this embodiment is, as shown in FIG. 3, a toric ion liquid member comprising a gelatinized ionic liquid, and is sandwiched between an outer tube body part 542m made of resin and an outer tube distal end part 542n made of resin. On a distal end side of the outer tube distal end part 542n formed are a plurality of (for example, three) cover parts 541n of an appentice shape to protect the glass response film 541s of the inner tube 541 from a mechanical contact with the outside.

At least one or more of quaternary ammonium cation, quaternary phosphonium cation and quaternary arsonium cation is used as a cation and at least one or more of $[R_1SO_2NSO_2R_2]^-$ (each of $R_1$, $R_2$ is a perfluoroalkyl group whose carbon number is 1~12 respectively), borate ion containing fluorine, bis (2-ethylhexyl) sulfosuccinate, $P(C_nF_{2n+1})_3F_3^-$, $(CF_3SO_2)_3C^-$, $AsF_6^-$, $SbF_6^-$, $(C_nF_{2n+1})SO_3^-$, and $(C_nF_{2n+1})COO^-$ is used as an anion for an ionic liquid.

In addition, gelatinization of the ionic liquid is conducted by a high polymer compound, and at least one compound selected from the group consisting of vinyliden fluoride-hexafluoropropylene copolymer, polymethyl methacrylate, polyacrylonitrile, polybutyl acrylate, and other synthetic rubber can be used as the high polymer compound.

A KCI solution (pH7) of high concentration (3.3 M) is contained as the internal liquid into the ion-selective electrode housing part S1 having the above arrangement and the internal electrode 51 for the ion-selective electrode and the temperature detecting element 53 are immersed into the internal liquid.

In addition, the KCI solution (pH7) is contained as the internal liquid into the reference electrode housing part S2 and the internal electrode 52 for the reference electrode is immersed into the internal liquid.

A lead wire is connected to each of the internal electrode 51 for the ion-selective electrode, the internal electrode 52 for the reference electrode and the temperature detecting element 53 in the composite electrode 5 respectively, and each lead wire is connected to the cable (C) and extends to the outside from the other end in an axial direction of the probe body 4 and then is connected to the device body 2. When the composite electrode 5 having this arrangement is immersed into or makes contact with the measurement sample whose ion concentration such as the pH is to be obtained, an electromotive force generates according to a difference of the ion concentration such as the pH between the internal liquid and the measurement sample, and the electromotive force appears as a potential difference between the internal electrode 51 for the ion-selective electrode and the internal electrode 52 for the reference electrode. Since the electromotive force fluctuates according to the temperature, the device body 2 calculates the corrections on the ion concentration such as the pH of the measurement sample and displays it with an output signal value of the temperature detecting element 53 as parameters in addition to the voltage difference.

Figure 4:
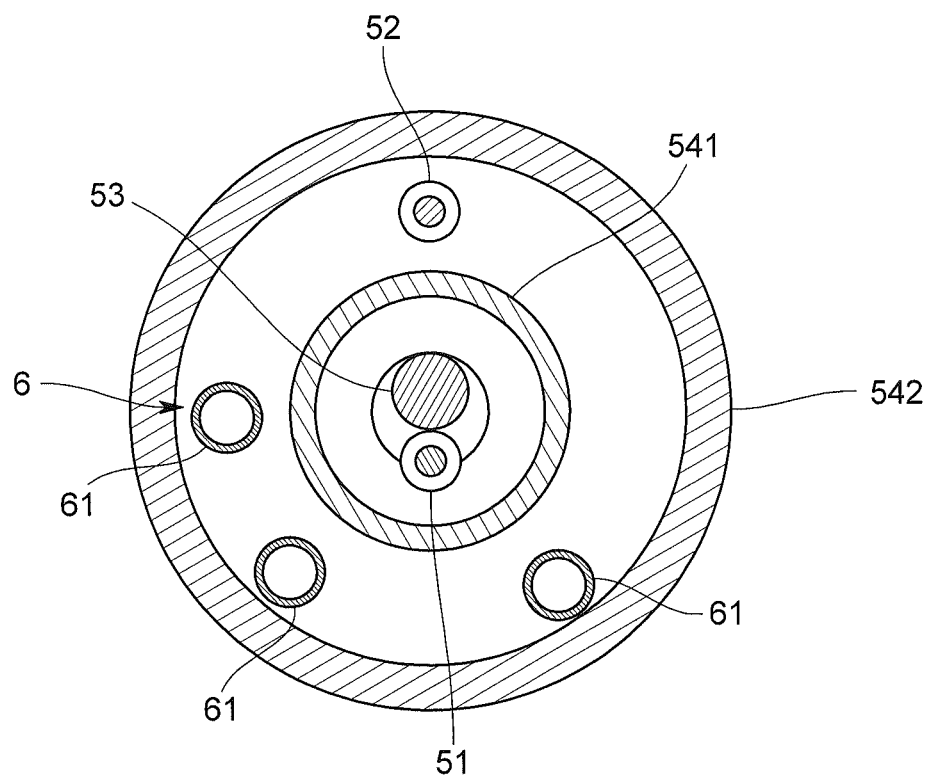
FIG. 4 is a cross-sectional view orthogonal to the axial direction of the composite electrode of this embodiment.

For the composite electrode 5 of this embodiment, a volume expansion absorption mechanism 6 that absorbs volume expansion of the internal liquid is arranged, as shown in FIG. 2 through FIG. 4, in the reference electrode housing part S2. The volume expansion absorption mechanism 6 is to absorb the volume expansion of the internal liquid due to congelation of the internal liquid in case that the composite electrode 5 is kept at a low temperature. For example, in case that the internal liquid housed in the reference electrode housing part S2 is a KCl solution whose concentration is lower than 3.3 M, since a coagulation point of the internal liquid approaches a zero point so that the internal liquid easily freezes, the volume expansion absorption mechanism 6 having this arrangement becomes especially useful.

The volume expansion absorption mechanism 6 is a hollow body 61 at least a part of which is immersed in the internal liquid and that has an elastic transform part that makes an elastic transformation in accordance with the volume expansion of the internal liquid and a gaseous layer arranged to make contact with the elastic transform part. The hollow body 61 of this embodiment is a bag-shaped elastic body inside of which a gaseous body such as air is filled.

The bag-shaped elastic body 61 is an elastic tube such as a rubber tube, for example, a polyimide tube, a heat shrinkable tube or a silicon tube in a generally cylindrical shape whose both ends are blocked. A hollow part of the bag-shaped elastic body 61 becomes the gaseous layer.

Concretely, the elastic body 61 is arranged to cover a sealed space in the reference electrode housing part S2 from one end part (a bottom end part as being a distal end part) thereof to the other end part (an upper end part as being a rear end part) thereof, and a part (refer to FIG. 2), for example, about two thirds of the elastic tube 61 is immersed in the internal liquid even though the composite electrode 5 stands, the elastic tube 61 floats in the internal liquid and the upper end of the elastic tube 61 makes contact with the upper part of the sealed space. At least a part of the elastic tube 61 immersed in the internal liquid serves as the elastic transform part.

In addition, one end part of the elastic tube 61 is arranged so as not to locate at an inner circumference side of the ion liquid member 55 so as not to prevent the ion liquid member 55 as being the ion conduction part from making contact with the internal liquid. In other words, as shown in FIG. 3, the reference electrode housing part S2 comprises a small diameter part S21 as being a part near an area where the ion liquid member 55 makes contact with the internal liquid and a big diameter part S22 that is formed at an upper part of the small diameter part S21 and where the internal electrode for the reference electrode 52 is housed, and the elastic tube 61 is arranged over a whole area in an axial direction of the big diameter part S22. In this embodiment shown is a case that a plurality of (three) elastic tubes 61 are arranged inside of the reference electrode housing part S2 (refer to FIG. 4), however, a number of the elastic tubes 61 may be other.

In accordance with the volume expansion absorption mechanism 6 having this arrangement, in case that a volume of the internal liquid expands due to congelation, the elastic transform part is pushed to the gaseous layer side by the volume expansion of the internal liquid and an amount of the expanded volume is absorbed by the gaseous layer. At this time, the gaseous layer is in a compressed state. Meanwhile, in case that the internal liquid melts, the elastic transform part returns to a state prior to congelation of the internal liquid due to an elastic restoring force of the elastic transform part and an inner pressure received by the gaseous layer.

In accordance with the ion concentration measuring device 100 in accordance with this embodiment having this arrangement, since the volume expansion of the internal liquid due to congelation of the internal liquid is absorbed by the volume expansion absorption mechanism 6, it is possible to prevent leakage of the internal liquid and breakage of the composite electrode 5. In addition, since the volume expansion absorption mechanism 6 is the elastic tube 61, it is possible to constitute the volume expansion absorption mechanism 6 just by inserting the elastic tube 61 into the reference electrode housing part S2 without providing a special processing on the support tube 54 made of glass.

The present claimed invention is not limited to the above-mentioned embodiment. For example, the composite electrode is explained in the above-mentioned embodiment, however, this invention may be applied to the reference electrode alone.

In addition, the ion conduction part is the gelatinized ionic liquid in the above-mentioned embodiment, however, it may comprise a liquid junction part comprising a porous body made of polyethylene or the like. With this liquid junction part, the reference electrode housing part can be considered to be the sealed space.

Furthermore, the ionic liquid is represented as the ion conduction part, however, the ion conduction part may be made of a material other than the ionic liquid as far as it is possible to obtain an electrical potential stability irrespective of the concentration of the internal liquid.

In addition, the volume expansion absorption mechanism comprises the hollow body separately arranged from the support tube as being the vessel, however, the volume expansion absorption mechanism may be integrally formed with the support tube by fixing the hollow body to the support tube (concretely, an inner surface of the outer tube or an outer surface of the inner tube).

Figure 5:
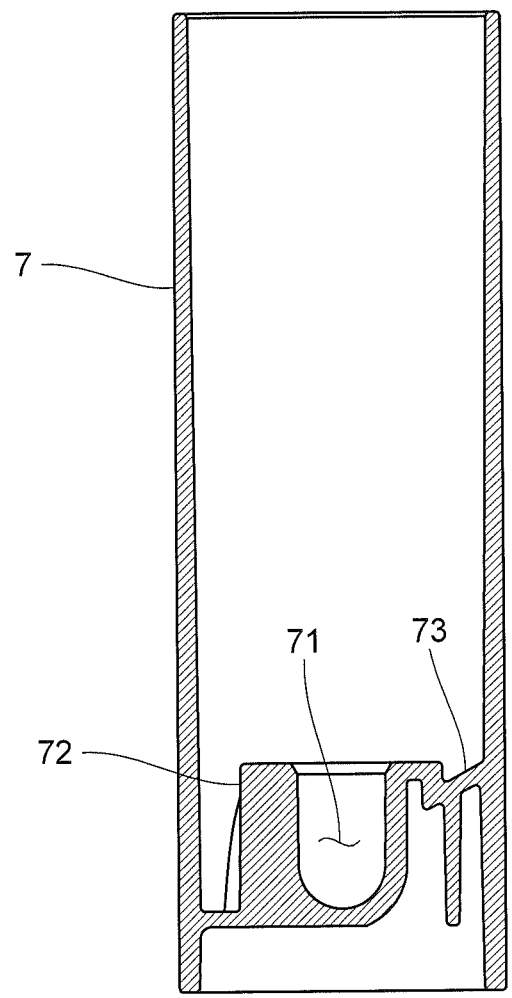
FIG. 5 is a cross-sectional view showing a sample vessel used for the composite electrode of this invention.

Furthermore, as shown in FIG. 5, the measurement sample may be measured by the use of a sample vessel 7 having a concavity-and-convexity structure corresponding to fill in a gap between the concavity-and convexity structure comprising the glass response film 541s and the cover part 542n1 locating at the distal end part of the composite electrode 5 together with the composite electrode 5. The sample vessel 7 is in a cylindrical shape having a bottom, and its internal diameter is set to be a little larger than an outer diameter of the composite electrode 5. On a center part of a bottom part of the sample vessel 7 provided is a sample store part 71 to store the measurement sample. The sample store part 71 is in a shape to correspond to the glass response film 541s and the glass response film 541s is immersed in the sample store part 71. In addition, a side wall 72 of the sample store part 71 is so arranged to fill in a space formed to surround the glass response film 541s. Furthermore, a concavity- and convexity part 73 to correspond to the cover part 542n1 is formed to surround the side wall 72 of the sample store part 71. In accordance with the sample vessel 7 having the above-mentioned arrangement, when the composite electrode 5 is inserted into the sample vessel 7 after the measurement sample is stored in the sample store part 71, the measurement sample stored in the sample store part 71 is pushed to outside of the sample store part 71 by the glass response film 541s and rises to the upper part along the gap between the composite electrode 5 and the sample vessel 7. With this rising movement, the measurement sample reaches the ion conduction part 55 of the composite electrode 5. In accordance with this arrangement, it is possible to reliably measure the ion concentration of the measurement sample, even though a liquid amount of the measurement sample is small.

In addition, it is a matter of course that the present claimed invention is not limited to the above-mentioned embodiment and may be variously modified without departing from a spirit of the invention.

EXPLANATION OF CODES

5 . . . composite electrode
52 . . . internal electrode for reference electrode
54 . . . support tube (vessel)
55 . . . ion conduction part (ion liquid member)
6 . . . volume expansion absorption mechanism
61 . . . elastic tube The invention claim is:
1. A reference electrode comprising:
a vessel that forms a sealed space,
an internal liquid that is contained in the vessel,
an internal electrode that is immersed in the internal liquid,
an ion conduction part that is arranged on a wall of the vessel and that electrically connects the internal liquid and a measurement sample, and
a volume expansion absorption mechanism at least a part of which is immersed in the internal liquid and that absorbs volume expansion of the internal liquid due to congelation of the internal liquid,
wherein the internal liquid contacts the exterior surface of the volume expansion absorption mechanism, and
wherein the volume expansion absorption mechanism comprises an elastic transform part that makes an elastic transformation in accordance with the volume expansion of the internal liquid and a gaseous closed layer that is arranged to make contact with the elastic transform part.

2. The reference electrode described in claim 1, wherein the volume expansion absorption mechanism is a hollow body inside of which a gas is filled,
the elastic transform part is formed as a part of a wall of the hollow body, and
the gaseous closed layer is provided in a hollow part of the hollow body.

3. The reference electrode described in claim 2, wherein the hollow body is a bag-shaped elastic body inside of which a gas is filled.

4. The reference electrode described in claim 3, wherein the bag-shaped elastic body is an elastic tube that both ends are blocked, and the elastic tube that is arranged from one end part of the sealed space in the vessel to the other end part thereof.

5. An ion concentration measurement device using the reference electrode described in claim 1.

\* \* \* \* \*